United States Patent [19]

Ciriza et al.

[11] 4,391,974

[45] Jul. 5, 1983

[54] WATER SOLUBLE CEPHADROXYL SALT

[75] Inventors: Santiago A. Ciriza; Carlos E. L. Padro, both of Barcelona, Spain

[73] Assignee: Liofilizaciones Esterilizaciones Y Sinthesis S.A., Barcelona, Spain

[21] Appl. No.: 220,286

[22] Filed: Dec. 29, 1980

[30] Foreign Application Priority Data

Feb. 5, 1980 [ES] Spain ............................ 488286

[51] Int. Cl.$^3$ ................ C07D 501/20; A61K 31/545
[52] U.S. Cl. ............................. 544/030; 424/246
[58] Field of Search ............... 544/261, 27, 30, 28; 424/246

[56] References Cited

U.S. PATENT DOCUMENTS

| | | | |
|---|---|---|---|
| 3,984,403 | 10/1976 | Fujisawa et al. | 544/30 |
| 4,254,029 | 3/1981 | Kaspi et al. | 544/30 |
| 4,299,955 | 11/1981 | Falciani et al. | 544/30 |
| 4,354,023 | 10/1982 | Falciani et al. | 544/30 |

*Primary Examiner*—Nicholas S. Rizzo
*Attorney, Agent, or Firm*—Scully, Scott, Murphy & Presser

[57] ABSTRACT

A new water soluble cephadroxyl salt and the process for the preparation thereof are disclosed.

1 Claim, No Drawings

WATER SOLUBLE CEPHADROXYL SALT

FIELD OF THE INVENTION

The present invention relates to a water soluble salt of cephadroxyl or 7-[D(−)-alpha-amino-alpha-(4-hydroxyphenyl)-acetamido]-3-methyl-3-cephem-4-carboxylic acid, having the formula:

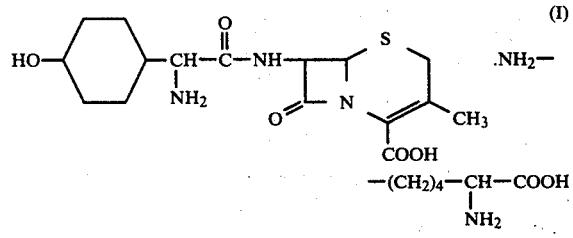

The invention also relates to a process for the preparation of the said water soluble salt.

SUMMARY OF THE INVENTION

7-[D(−)-alpha-amino-alpha-(4-hydroxyphenyl)-acetamido]-3-methyl-3-cephem-4-carboxylic acid is a known antibiotic having a broad antibacterial spectrum. Cephadroxyl, another name under which the above acid is known, has a solubility in water of about 0.01 g/ml, which is a disadvantage for its application by intramuscular injection. On the contrary, the salts formed with certain amino acids and, particularly, the lysine salt are highly soluble in water, in excess of 0.25 g/ml and are well tolerated in intramuscular and endovenous injection.

Half a minute after endovenous injection of a soluble cephadroxyl lysine salt to albino rats at a rate of 25 mg of active cephadroxyl per 1 Kg body weight of the animal, levels of 213 μg/ml were obtained and therapeutically significant levels were still maintained 5 hours after administration.

Similar experiments have been carried out at the same dose levels and with the same animals, using intramuscular injection and maximum levels of 53.16 μg/ml were obtained 15 minutes after injection and therapeutically significant values were still maintained even 8 hours after administration.

The pharmacokinetics of both endovenous and intramuscular injections in the rat shows a good adjustment to a bicompartmental model and a good bioavaliability of around 95% in the case of intramuscular injection, the endovenous injection being taken as 100%.

The results obtained with these two forms of injection and the high maximum levels of 213 μg/ml and 53.6 μg/ml are of extraordinary interest when compared with those obtained with the oral administration of cephadroxyl monohydrate at the same active ingredient levels and to the same animal, since the maximum levels obtained are only 17.28 μg/ml 45 minutes after administration.

The obvious advantages of having an antibiotic which may be administered either endovenously or intramuscularly and which gives extraordinarily high active antibiotic blood levels are of great interest for their possible therapeutic use in comparison with products which may be administered only orally and which reach maximum blood levels of only 30% of the level obtained by intramuscular administration and 7% of the level obtained by endovenous administration.

The process according to the invention is characterised fundamentally by reacting cephadroxyl of the formula:

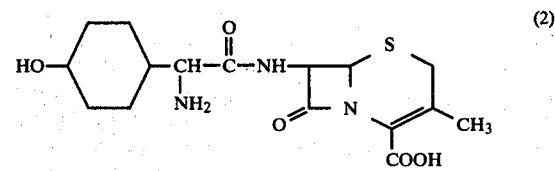

with an equimolecular amount of lysine of the formula:

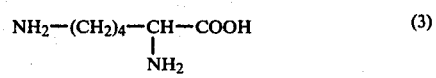

the soluble salt being isolated thereafter.

The reaction is conducted in an aqueous or aqueous and alcoholic medium.

The isolation of the product prepared in aqueous solutions is effected by lyophilisation, whereas the product prepared in aqueous and alcoholic solutions is isolated by precipitation by way of other alcoholic or ketonic solvents, preferably ethanol or acetone, subsequent separation of the precipitate by filtration or centrifugation and final drying under vacuum. Since the product is for use in injections, it is absolutely necessary for all the solutions to be filtered through sterilizing filters prior to isolation of the product, either by lyophilisation or by precipitation or the non sterile product produced should be sterilised by other conventional methods.

EXAMPLE I 14.3 g of cephadroxyl were suspended in 74.3 cc of bidistilled water, without the temperature exceeding 10° C. at any time. Thereafter 11.4 g of a 50% L-lysine aqueous solution were added over 30 minutes, the above temperature range being maintained. After addition, stirring was maintained for 10 minutes and the pH is adjusted to 8.56. Thereafter, the product is filtered with a sterilising filter, is frozen in a tray and lyophilised to give 17.5 g of ground dry sterile product, perfectly soluble in water at a rate in excess of 1 g in 4 c.c.s.

Melting point: 210°–215° C.
$[\alpha]_D^{20°} (c=1) = 109.5°$.
$I_2$ valuation = 90%.

EXAMPLE II

A suspension of 4 g of cephadroxyl in 12 c.c. of bidistilled water was prepared, at a temperature below 7° and 3.2 g of a 50% aqueous solution of lysine was added over 15 minutes. At the end of the addition, the clear solution was poured over 200 c.c. of a 1:1 mixture of ethanol and acetone. The pouring time was approximately 60 minutes. In this way a creamy white product was precipitated out, which was left to cool for 25 minutes, with intermittent interruption of the stirring to facilitate crystallisation.

At the end of this period, the precipitate was filtered, washed with abundant acetone and dried in a muffle under vacuum at a temperature of from 30° C. to 40° C. A creamy white product having a melting point of 210°–212° C., specific rotation 100° and iodometric valuation 83% was obtained.

EXAMPLE III 8 g of cephadroxyl were suspended in 50 c.c. of methanol at a temperature below 10° C. and 6.4 g of a 50% aqueous solution of lysine were added over 15 minutes. At the end of this time, the temperature was raised to 15°–20° C., stirring was continued for 15 minutes and the mixture was cooled, being filtered thereafter through a sterilising filter. The filtered solution was poured over a mixture of 70 c.c. absolute ethanol and 30 c.c. hexane, previously filtered through a sterilising filter. Thus a white precipitate appeared which was stirred for 15 minutes. It was filtered in a sterile area and washed with 25 c.c. of sterile absolute ethanol and 25 c.c. of sterile hexane, successively. The filtered solid was dried at 40° C. under vacuum to give 10.5 g of dry white product.

The infra red spectrum of the product obtained shows characteristic bands of 2800, 3500, 2595, 1755, 1580, 1500 and 840 cm$^{-1}$.

EXAMPLE IV 80 g of cephadroxyl were suspended in 400 c.c. of methanol at a temperature of 5° C. and a 52% aqueous solution of lysine (58.2 g) was added over 30 minutes. Stirring was continued for 15 minutes, and the temperature was allowed to rise to 10° C. The resulting solution was filtered through a sterilising filter and poured over 1.0 liter of sterile filtered absolute ethanol. In this way a white solid was precipitated out and was left under stirring for 15 minutes, after which, it was filtered in a sterile area, the solid being dried under vacuum at a temperature lying between 30° and 40° C.

Thus 100 g of white product, having a melting point of 215°–218° C.; $[\alpha]_D^{20}$ (c=1)=114° and a iodometric valuation of 94% were obtained. The NMR spectrum was:

| P.P.M. | Relative Int. | Multiplicity | Assignation |
|---|---|---|---|
| 1.62 | | | H—C |
| 1.73 | 6 | Multiplet | H—B |
| 1.84 | | | H—D |
| 1.88 | 3 | Singlet | H—9 |
| 2.90 | 2 | Triplet | H—H |
| 3.08 | 2 | Quartet AB | H—2 |
| 3.71 | 1 | Triplet | H—E |
| 4.41 | — | Doublet | NH$_2$ |
| 4.64 | 1 | Singlet | H— |
| 4.73 | — | Singlet | H$_2$O |
| 4.95 | 1 | Doublet | H—7 |
| 7.11 | 4 | | —C$_6$—H$_4$— |

What we claim is:

1. A water soluble salt of cephadroxyl or 7-[D(−)-alpha-amino-alpha-(4-hydroxyphenyl)-acetamido]-3-methyl-3-cephem-4-carboxylic acid having the formula:

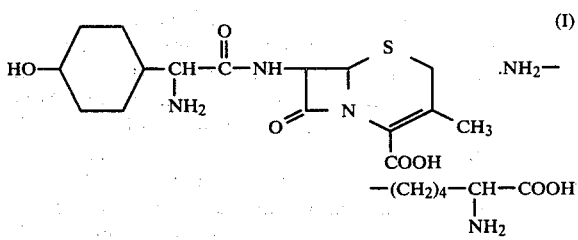

* * * * *